(12) United States Patent
Capuzzi et al.

(10) Patent No.: US 11,400,036 B2
(45) Date of Patent: *Aug. 2, 2022

(54) AQUEOUS COSMETIC COMPOSITIONS CONTAINING PELARGONIC ACID ESTERS

(71) Applicant: Novamont S.p.A., Novara (IT)

(72) Inventors: Luigi Capuzzi, Novara (IT); Francesca Digioia, Barengo (IT); Vanessa Bramati, Lainate (IT); Federica Carlomagno, Saronno (IT); Alessandra Cominetti, Agnadello (IT)

(73) Assignee: NOVAMONT S.P.A., Novara (IT)

(*) Notice: Subject to any disclaimer, the term of this patent is extended or adjusted under 35 U.S.C. 154(b) by 24 days.

This patent is subject to a terminal disclaimer.

(21) Appl. No.: 15/758,076

(22) PCT Filed: Sep. 7, 2016

(86) PCT No.: PCT/EP2016/071079
§ 371 (c)(1),
(2) Date: Mar. 7, 2018

(87) PCT Pub. No.: WO2017/042213
PCT Pub. Date: Mar. 16, 2017

(65) Prior Publication Data
US 2018/0207071 A1    Jul. 26, 2018

(30) Foreign Application Priority Data
Sep. 8, 2015   (IT) ................... 102015000049538

(51) Int. Cl.
| *A61K 8/37* | (2006.01) |
| *A61K 8/06* | (2006.01) |
| *A61Q 5/12* | (2006.01) |
| *A61Q 19/08* | (2006.01) |
| *A61Q 19/00* | (2006.01) |
| *A61Q 17/04* | (2006.01) |
| *A61Q 1/10* | (2006.01) |

(52) U.S. Cl.
CPC ............... *A61K 8/37* (2013.01); *A61K 8/06* (2013.01); *A61K 8/375* (2013.01); *A61Q 1/10* (2013.01); *A61Q 5/12* (2013.01); *A61Q 17/04* (2013.01); *A61Q 19/00* (2013.01); *A61Q 19/08* (2013.01)

(58) Field of Classification Search
CPC . A61K 8/37; A61K 8/375; A61K 8/06; A61K 8/062; A61Q 1/10; A61Q 5/12; A61Q 17/04; A61Q 19/00; A61Q 19/08
See application file for complete search history.

(56) References Cited

U.S. PATENT DOCUMENTS

| 5,254,331 A * | 10/1993 | Mausner ................. A61K 8/44 424/401 |
| 7,875,263 B1 | 1/2011 | O'Lenick |
| 2003/0091526 A1* | 5/2003 | Kaba ........................ A61K 8/37 424/70.14 |
| 2005/0196347 A1* | 9/2005 | Berillouet ................. A61K 8/06 424/47 |
| 2008/0268003 A1* | 10/2008 | Thevenet ................. A61K 8/02 424/401 |
| 2015/0011654 A1* | 1/2015 | Von Der Fecht ...... A61K 8/375 514/738 |
| 2015/0209429 A9* | 7/2015 | Lathrop ................. A61K 47/14 514/172 |
| 2016/0296430 A1* | 10/2016 | Das ......................... A61K 8/06 |

FOREIGN PATENT DOCUMENTS

| JP | S552648 A | 1/1980 |
| JP | S59190907 A | 10/1984 |
| JP | 2013035799 A | 2/2013 |
| WO | WO 94/007460 A1 | 4/1994 |
| WO | WO-2014197398 A1 * | 12/2014 ........... A61K 9/0014 |

OTHER PUBLICATIONS

"SIMULSOL™ 165," Seppic, <https://www.seppic.com/simulsol-165>, Copyright 2019, p. 1-2.*
"Sunscreen SPF 50+", GNPD, Mintel; Oct. 31, 2012; XP-002753094.
"Bb. Shine On (and On . . . ) Finishing Spray", GNPD, Mintel; Jun. 30, 2011; XP-002753095.
First office action dated Sep. 8, 2020 of JP 2018-512378,. counterpart Japanese application, partial English translation.

* cited by examiner

*Primary Examiner* — Michael P Cohen
(74) *Attorney, Agent, or Firm* — Polsinelli PC

(57) ABSTRACT

Aqueous cosmetic compositions comprising at least 20% by weight of an aqueous component and a lipophilic component characterized in that the lipophilic component comprises at least one ester selected from neopentylglycol dipelargonate, glycerol tripelargonate, pentaerythritol tetrapelargonate or mixtures thereof.

19 Claims, No Drawings

AQUEOUS COSMETIC COMPOSITIONS CONTAINING PELARGONIC ACID ESTERS

CROSS REFERENCE TO RELATED APPLICATIONS

This application is a National Phase filing under 35 U.S.C. § 371 of PCT/EP2016/071079 filed on Sep. 7, 2016; and this application claims priority to Application No. 102015000049538 filed in Italy on Sep. 8, 2015 under 35 U.S.C. § 119. The entire contents of each application are hereby incorporated by reference.

This invention relates to aqueous cosmetic compositions containing one or more esters selected from neopentyl glycol dipelargonate, glycerol tripelargonate and pentaerythritol tetrapelargonate.

In the cosmetics sector increasing attention is being paid to the identification of new ingredients having a low environmental impact, of natural and renewable origin and at the same time provided with excellent functional and sensory properties.

Among cosmetic compositions, aqueous compositions may be for example in the form of water-based emulsions (O/W), oil-based emulsions (W/O), microemulsions or water-lipid dispersions. These are used in care of the skin, of the hair, in make-up and in hygiene products and together with a hydrophilic component may have a lipophilic component which, depending on the product, helps to ensure optimal detergency, hydration, resistance to water and softness.

It has now been observed that esters of pelargonic acid obtainable from renewable sources with polyols such as neopentyl glycol, glycerol and pentaerythritol, used alone or in a mixture, have special lubricating and plasticising capabilities within the composition and are capable of providing the skin with a soft and smooth appearance because of their emollient and film-forming properties; they are also capable of keeping the skin hydrated because of their ability to form a barrier which slows down the loss of water from the skin. They also have an excellent ability to solubilise and disperse sun filters, pigments, active agents and other additives.

The excellent properties of softness and softness of touch which distinguishes them makes them particularly suitable for use, in mixtures or alone, as ingredients of the lipophilic component in aqueous compositions for cosmetic use, i.e. for the preparation of products intended for application to the outer surface of the human body (epidermis, lips and cutaneous annexes) in order exclusively or mainly to clean them, perfume them, modify their appearance, protect them, maintain them in a good condition or correct body odours.

The object of this invention is therefore aqueous cosmetic compositions comprising at least 20% by weight of an aqueous component and a lipophilic component characterised in that the said lipophilic component comprises at least one ester selected from neopentyl glycol dipelargonate, glycerol tripelargonate, pentaerythritol tetrapelargonate or mixtures thereof. The said cosmetic compositions preferably contain more than 30%, more preferably more than 35%, and even more preferably more than 50%, by weight of the aqueous component. Compositions comprising at least two esters selected from neopentyl glycol dipelargonate, glycerol tripelargonate, pentaerythritol tetrapelargonate are preferred.

According to one aspect of the present invention, aqueous cosmetic compositions whose lipophilic component comprises at least one of glycerol tripelargonate and pentaerythritol tetrapelargonate are preferred; among these, those comprising glycerol tripelargonate are more preferred.

The said ester selected from neopentyl glycol dipelargonate, glycerol tripelargonate and pentaerythritol tetrapelargonate is present in quantities of preferably between 0.1% and 50% by weight, preferably between 0.1% and 35% by weight, with respect to the weight of the cosmetic composition.

According to one advantageous aspect of the invention, the said esters (neopentyl glycol dipelargonate, glycerol tripelargonate and pentaerythritol tetrapelargonate) are prepared from pelargonic acid from a renewable source, obtained for example through processes for the oxidative cleavage of vegetable oils, fatty acids and their derivatives, whether modified or not. Preferred examples of renewable sources of pelargonic acid are the vegetable oils from sunflowers, brassicaceae or thistles (such as *Cynara cardunculus* and *Silybum marianum*). Particularly preferred sources of pelargonic acid are vegetable oils with a high oleic or erucic acid content.

The said pelargonic acid is preferably obtained through oxidative cleavage processes in which inorganic and organic peroxides, peracids, nitric acid, permanganates, periodates, $O_2$, $O_3$ or their gaseous mixtures are used as oxidising agents.

Oxidative cleavage processes in which peroxides, such as hydrogen peroxide, and $O_2$ or mixtures containing $O_2$ are used as oxidising agents are preferred. Specific examples are the oxidative cleavage processes described in applications WO 94/10122, WO 07/039481, WO 2008/138892, WO 2011/080296, WO 2011/080297 or WO 2013/079849.

According to a preferred aspect of the invention, the said esters are prepared from pelargonic acid of high purity, preferably more than 95%, preferably more than 98%, and a polyol selected from neopentyl glycol, glycerol or pentaerythritol, through an esterification reaction which is advantageously performed in the absence of catalyst.

The said esterification is advantageously performed in the presence of a molar excess of pelargonic acid with respect to the moles of polyol, preferably 30% or more and less than 70%, operating at temperatures typically between 180 and 240° C., preferably at 200-210° C. The water forming during the esterification reaction is advantageously removed from the reaction environment, for example by applying a gradual reduction in pressure; at the end of the reaction the excess acid is removed, preferably through evaporation. The ester so obtained may advantageously undergo purification treatments according to processes known to those skilled in the art, for example using activated carbon agents and/or decolouring earths, with a view to removing any colour, odour and residual activity. Examples of decolouring earths which may be used, including in combination with activated carbon agents, are Grade F-118FF, Grade F76 (marketed by BASF), Minclear N100, Minclear E100 or Pansil 2 (marketed by Tolsa).

In comparison with esters obtained through ordinary esterification procedures catalysed by metals, for example tin, the esters obtained by operating according to the above-mentioned procedure do not contain metal residues which might have an effect on the organoleptic properties (e.g. colour, odour) and stability of the finished cosmetic products and on their toxicological properties. They therefore have the particular advantage of a low inorganic matter content and require simplified preliminary treatments for use in the cosmetics environment.

The aqueous cosmetic compositions according to the invention may have a variable content of the lipophilic component. In addition to the esters of pelargonic acid specified above (neopentyl glycol dipelargonate, glycerol tripelargonate, pentaerythritol tetrapelargonate), the said lipophilic component may comprise one or more oils selected from esters, ethers, amides, alcohols and hydrocarbons of natural and/or synthetic origin, silicone oils or their mixtures. The said oils are typically in liquid form at ambient temperature (25° C.) and atmospheric pressure.

Possible examples of esters of natural origin are triglycerides of saturated or unsaturated fatty acids, such as for example triglycerides of C8 and C10 acids, or their mixtures such as for example those present in vegetable oils. Suitable vegetable oils are for example olive oil, sunflower oil, maize oil, soya oil, castor oil, apricot oil, avocado oil, almond oil, macadamia oil, jojoba oil or karite oil.

Esters of synthetic origin are for example esters of linear and branched carboxylic acids with monoalcohols, such as isononyl isononanoate, isopropyl myristate, 2-ethy hexyl palmitate, isodecyl neopentanoate, isostearyl neopentanoate, 2-octyldodecyl stearate, 2-octyldodecyl erucate or isostearyl isostearate, diisostearyl maleate, C12-15 alkyl benzoate; esters of C7-C10 chain fatty acids with fatty alcohols; hydroxylated esters, such as isostearyl lactate, octyl hydroxystearate, octyldodecyl hydroxystearate; esters of polyols, such as propylene glycol dioctanoate, neopentyl glycol diheptanoate or diethylene glycol diisononanoate and pentaerythrityl tetraisostearate.

One example of an ether is dicaprilyl ether. One example of an amide is dibutyl lauroyl glutamide.

Other examples of oils include fatty alcohols such as octyldodecanol, hexyldodecanol, isostearyl alcohol.

Hydrocarbon oils of natural origin are for example terpene hydrocarbons such as squalene and squalane; hydrocarbon oils of mineral or synthetic origin are for example liquid paraffin and its derivatives such as isoparaffins (e.g. isododecane, isohexadecane, polydecene hydrogenate) and cycloparaffins.

The silicone oils are synthetic compounds based on silicon; they may be volatile or non-volatile, linear or cyclic. Examples of silicone oils are polysiloxanes and their derivatives comprising for example alkyl, alkoxyl or phenyl groups; silicone oils typically used include the polydimethylsiloxanes (Dimethicone), Amodimethicone, Cyclomethicones such as Cyclopentasiloxane and Cyclohexasiloxane, Amino Bispropyl Dimethicone, Aminopropyl Dimethicone, Amodimethicone hydroxystearate, Behenoxy-Dimethicone, C30-45 Alkyl Dimethicone, C24-28 Alkyl Dimethicone, C30-45 Alkyl Methicone, Cetearyl Methicone, Cetyl Dimethicone, Dimethoxysilyl Ethylenediaminopropyl Dimethicone, Hexyl Methicone, Hydroxypropyldimethicone, Stearamidopropyl Dimethicone, Stearoxy Dimethicone, Stearyl Methicone, Stearyl Dimethicone and Vinyl Dimethicone.

The lipophilic component of the cosmetic compositions according to the invention may also comprise one or more components in solid or pasty form at ambient temperature (25° C.) and atmospheric pressure, such as butters and/or waxes. The said components impart body, viscosity, film-forming and barrier properties to the cosmetic compositions containing them, such as for example creams, milks, serums. These too may be of plant, animal, mineral and/or synthetic origin.

By the term "butters" are meant all those substances comprising a high fraction of triglycerides responsible for the emollient, hydrating and regenerating properties of the skin barrier. They may contain a proportion of insaponifiable fraction, rich for example in terpene alcohols, phytosterols, tocopherols and hydrocarbons. Examples are Karite butter, cocoa butter, cupuacu butter.

Suitable waxes are the waxes typically used in cosmetic compositions, and may be of natural and/or synthetic origin. Examples of natural waxes are beeswax or cera alba, carnauba wax, candelilla wax, Japan wax, rice wax, waxes deriving from hydrogenated oils such as jojoba oil or sunflower oil or coconut oil, esters of saturated long chain fatty acids with long chain monoalcohols or their glycerides, such as cetyl palmitate, cetyl stearate, palmitic and stearic triglycerides.

Examples of mineral or synthetic waxes are lignite wax, microcrystalline wax, paraffin, ozokerite, ceresin, synthetic beeswax, lanolin and their ethers with polypropylene glycol, polyethylene waxes, esters of fatty acids having a melting point above 25° C., cetyl esters and polyamides. Silicone waxes may also be used, such as alkyl or alkoxy dimethicones or poly(di)methylsiloxanes of high molecular weight.

Advantageously the lipophilic component of the cosmetic compositions according to the invention comprise one or more components deriving from the insaponifiable fraction of vegetable oils (for example carotenoids, xanthophylls, tocopherols, phytosterols, aliphatic and terpene alcohols). Vitamins and active agents of a lipophilic nature may also be present dissolved in the lipophilic component.

Aqueous compositions according to the invention may be for example in the form of oil-based emulsion (water in oil emulsions, W/O), water-based emulsions (oil in water emulsions, O/W) and may take the form of multiple emulsions (for example W/O/W and O/W/O).

A preferred embodiment of the invention relates to cosmetic compositions in the form of oil-based emulsion in which the continuous phase is lipophilic. The said compositions preferably comprise up to 50% by weight, preferably up to 35% by weight, and even more preferably up to 25% by weight of the said lipophilic component comprising at least one ester selected from neopentyl glycol dipelargonate, glycerol tripelargonate and pentaerythritol tetrapelargonate and their mixtures. In addition to the abovementioned esters according to the invention the lipophilic component of the said oil-based emulsions advantageously comprises at least one oil from those listed above, for example a silicone oil. A preferred example of oil-based emulsions according to this invention is silicone-based emulsions (W/Si) in which the lipophilic component comprises one or more silicone oils and one or more of the esters of pelargonic acid specified above.

According to a particularly preferred aspect the said aqueous cosmetic compositions in the form of oil-based emulsions comprise, with respect to the total weight of the cosmetic composition:

(a) from 35 to 80% by weight, preferably from 50 to 80% by weight, of an aqueous phase;

(b) from 10% to 50%, preferably from 10 to 35% of a lipophilic component comprising at least one ester selected from neopentyl glycol dipelargonate, glycerol tripelargonate and pentaerythritol tetrapelargonate or their mixtures;

(c) from 0.3% to 15% of one or more emulsifying agents with an HLB of preferably between 3 and 6.

Typically the said aqueous phase comprises from 60 to 80% by weight of the cosmetic composition and the said lipophilic component comprises 25-35% by weight.

The said aqueous phase may contain chelating agents such as for example ethylenediamine tetraacetic acid and its sodium salts (e.g. disodium, trisodium and tetrasodium salts), sodium chloride, magnesium sulfate and other stabilising agents, preservatives, active ingredients and hydrating agents.

Preferably the lipophilic component of the compositions in the form of oil-based emulsion according to the invention comprises, or advantageously consists of, pentaerythritol tetrapelargonate or its mixtures with glycerol tripelargonate or with neopentyl glycol dipelargonate and glycerol tripelargonate.

According to this embodiment the compositions in the form of oil-based emulsion are suitable for example for the preparation of creams, sun creams, serums, foundation creams, concealers and mascara.

Another preferred embodiment of the invention relates to compositions in the form of water-based emulsion in which the continuous phase is hydrophilic. The said compositions preferably comprise up to 40% by weight, preferably up to 20% by weight, even more preferably up to 15% by weight, of a lipophilic component comprising at least one ester selected from neopentyl glycol dipelargonate, glycerol tripelargonate and pentaerythritol tetrapelargonate and their mixtures.

According to a particularly preferred aspect the said aqueous cosmetic compositions in the form of water-based aqueous emulsions comprise, with respect to the total weight of the cosmetic composition:

(a) from 60 to 90% by weight of an aqueous phase;
(b) from 0.5% to 40%, preferably from 1 to 20% and preferably from 1 to 15%, of a lipophilic component comprising at least one ester selected from neopentyl glycol dipelargonate, glycerol tripelargonate and pentaerythritol tetrapelargonate or their mixtures;
(c) from 5% to 15% of one or more emulsifying agents with an HLB of preferably between 6 and 12.

Preferably the lipophilic component of the compositions in the form of water-based emulsion according to the invention comprises, or advantageously consists of, neopentyl glycol dipelargonate or glycerol tripelargonate or mixtures of neopentyl glycol dipelargonate and glycerol tripelargonate or mixtures of neopentyl glycol dipelargonate and pentaerythritol tetrapelargonate.

According to this embodiment the compositions in the form of water-based emulsion are suitable for example for the preparation of creams, milks, serums, butters, sun creams, hair products such as conditioners, colouring agents, leave-ons and make-up products such as foundation creams, mascaras, concealers and lipsticks.

Typical emulsifying agents or emulsifiers used in compositions according to the invention have long or medium-length alkyl chains (generally longer than C12), and may be anionic, cationic, amphoteric or non-ionic.

The said emulsifying agents may be selected for example from the group comprising monoglycerides of fatty acids, sorbitan esters (for example monoesters, diesters, triesters and their mixtures) which may optionally be ethoxylated, saccharose esters, protein condensates with fatty acids, polyglycerols and/or their esters with fatty acids, ethers of glucose and/or polyglucose with fatty alcohols, lecithin and/or hydrogenated lecithin, ethoxylated fatty alcohols, ethoxylated fatty acids (for example PEG-100 stearate), soaps such as triethanolamine stearate, ethoxylated and non-ethoxylated phosphoric esters (for example potassium cetyl phosphate).

Emulsifying agents suitable for oil-based emulsions typically have unsaturated, branched or substituted alkyl chains, such as for example the oleic, isostearyl, ricinoleic and hydroxystearyl chains.

Emulsifying agents suitable for water-based emulsions typically have saturated and linear chains, such as for example stearyl and palmitoleic chains.

According to another preferred aspect of the invention the said aqueous compositions comprise up to 15% by weight, preferably up to 10% and more preferably up to 5% by weight of a lipophilic component comprising at least one ester selected from neopentyl glycol dipelargonate, glycerol tripelargonate and pentaerythritol tetrapelargonate and their mixtures. The said aqueous cosmetic compositions preferably comprise, with respect to the total weight of the cosmetic composition:

(a) from 60 to 90% by weight of an aqueous component;
(b) from 0.5% to 15%, preferably from 1 to 10%, preferably from 1 to 5% by weight of a lipophilic component comprising at least one ester selected from neopentyl glycol dipelargonate, glycerol tripelargonate and pentaerythritol tetrapelargonate or their mixtures;
(c) from 8% to 40% of one or more surfactants.

Advantageously aqueous compositions according to this aspect of the invention comprise a quantity of ester selected from neopentyl glycol dipelargonate, glycerol tripelargonate and pentaerythritol tetrapelargonate or their mixtures comprising between 0.1 and 12% by weight, preferably between 0.1 and 6% by weight of the lipophilic component.

Among such compositions those preferred are those in which the lipophilic component comprises neopentyl glycol dipelargonate, glycerol tripelargonate or their mixtures.

According to this aspect of the invention the said aqueous compositions may advantageously be in the form of microemulsion; they are suitable for example for the preparation of bath foam, shower foam, detergents, shampoos, leave-on products and liquid soaps.

In such aqueous cosmetic compositions the said surfactants have the function of reducing surface tension, encouraging detergency; they may or may not have a foam-generating function and may be non-ionic, anionic, amphoteric or cationic.

Typical surfactants used in compositions according to the invention typically have short or medium-length alkyl chains (generally shorter than C14), such as for example those of capric, caprylic and lauric acids.

They may be selected for example from the group comprising: alkyl sulfates and/or alkyl ether sulfates, preferably of Na, Mg, Zn or ammonium (NH4), monoethanolamine (MEA), triethanolamine (TEA) or monoisopropylamine (MIPA); alkyl ether carboxylates; protein condensates with fatty acids; acyl glutamates; acyl sarcosinates; acyl isothionates; acyl methyl taurates; alkyl sulfosuccinates; soaps; alkyl betaine and alkylamidopropyl betaine; alkyl and alkylamidohydroxy sultaine; alkyl amphoacetates and alkyl amphodiacetates; alkyl amphopropionates and alkyl amphodipropionates; alkyl and alkylamidopropyl aminoxides; polysorbates (e.g. polysorbate 20); monosaccharose esters; alkyl glucosides; quaternary ammonium salts.

Those skilled in the art will readily be able to determine the quantity of surfactant required on the basis of the type of cosmetic product for which the composition is intended. For example, cosmetic compositions intended for the preparation of intimate detergents typically contain a quantity of surfactants comprising from 8 to 10% by weight; shampoos from 10 to 15% by weight; shower foam from 13 to 18% by weight, and bath foam from 18 to 22% by weight. According to another preferred aspect of the invention the said aqueous cosmetic compositions are in biphasic form, or have the aqueous phase separate from the lipophilic phase in two separate layers. Cosmetic products prepared with such compositions typically require mixing before use, which brings about the formation of temporary emulsions.

Preferably the said compositions comprise, with respect to the total weight of the cosmetic composition:

(a) from 50 to 70% by weight of an aqueous phase;
(b) from 30% to 50% of a lipophilic phase comprising at least one ester selected from neopentyl glycol dipelargonate, glycerol tripelargonate and pentaerythritol tetrapelargonate or their mixtures.

Preferably the said compositions in two-phase form according to the invention comprise a quantity of ester selected from neopentyl glycol dipelargonate, glycerol tripelargonate and pentaerythritol tetrapelargonate or their mixtures comprising between 0.1 and 50% by weight, preferably between 0.1 and 30% by weight, even more preferably between 0.1 and 10% by weight, of the lipophilic component.

Compositions whose lipophilic component comprises neopentyl glycol dipelargonate or glycerol tripelargonate or a mixture of neopentyl glycol dipelargonate and glycerol tripelargonate or a mixture of neopentyl glycol dipelargonate and pentaerythritol tetrapelargonate are preferred.

In addition to the abovementioned esters of pelargonic acid, the said lipophilic phase preferably comprises mineral and/or silicone oils, for example isododecanes, cyclopentasiloxane, products of the reaction between propylene oxide and stearyl alcohols (such as polypropyleneglycol-15 stearyl ether) or vegetable oils such as almond, olive and jojoba oils.

According to this aspect the compositions in the form of aqueous two-phase solution are suitable for example for the preparation of products for the removal of make-up.

According to a preferred aspect the aqueous cosmetic compositions according to this invention also comprise one or more sun filters, in quantities of preferably between 0.05% and 35% by weight, preferably between 0.1 and 25%, with respect to the weight of the cosmetic composition.

Sun filters have the function of protecting skin and/or hair from UVA/UVB radiation. These include for example filters or physical screens with reflecting properties such as for example zinc oxide and titanium dioxide, either in the form of nanomaterials or having particles of larger size, silica, kaolin, iron and/or magnesium oxides, and chemical filters, typically organic molecules capable of absorbing and converting the energy of ultraviolet radiation such as cinnamates, benzoimidazoles, benzophenones, benzylidene camphorate, PABA and its derivatives, salicylates, anthranylates, dibenzoyl methanes, octocrylene, triazines such as octyltriazone, bis-ethylhexyloxyphenol methoxyphenyl triazine and diethyl hexyl butamido triazone, natural antioxidants such as vitamin C and vitamin E or synthetic vitamins, such as Tinogard TT, or their combinations.

Physical and chemical filters may be of natural origin (such as for example gamma orizanol) or synthetic, and be used alone or more advantageously in combination.

Specific examples of sun filters suitable for use in the compositions according to the invention are octyl-methoxycinnamate, 2-ethyl-hexyl-4-dimethylaminobenzoate, butylmethoxydibenzoylmethane, octyl triazone, diethyl hexylbutamido triazone, ethyl hexyl salicylate, zinc oxide, titanium dioxide, or their combinations.

According to a particularly preferred embodiment the cosmetic composition according to the invention take the form of an emulsion and comprise, with respect to the total weight of the composition, from 0.1 to 35% by weight, preferably from 1 to 25, preferably from 1 to 10% by weight of at least one sun filter.

Because of the characteristics of the esters of pelargonic acid in the oily component, the cosmetic compositions according to the invention have the particular advantage of ensuring optimum dispersion and/or solubilisation of the sun filters, and may increase the stability of the emulsion and help to increase their protection factor. Additionally, they have shown a higher solubilisation and dispersion rates when compared to some of the commonly used oily solvents/dispersants. They are therefore suitable for the preparation of cosmetics for the care of the body and hair and make-up products having a protective and anti-aging function.

Compositions comprising pentaerythritol tetrapelargonate and glycerol tripelargonate or their mixtures, which have particular softness, are particularly suitable for this purpose. Compositions comprising pentaerythritol tetrapelargonate are more preferred.

According to a preferred aspect the cosmetic composition according to the invention advantageously comprises one or more colouring agents or dyes, in a quantity of preferably between 0.1% and 35% by weight, more preferably of between 0.1 and 30% by weight, even more preferably between 0.1 and 20% by weight. The said colouring agents may be soluble or insoluble in water, soluble or insoluble in fats, mineral or organic, natural or synthetic, and have the function of colouring or opacifying the cosmetic composition. Examples of suitable colouring agents are pigments, lacquers or pearls, which may be used as such or after surface treatments intended for example to modify waterrepellence or hydrophilic properties. The pigments include derivatives of metals of an inorganic nature, for example oxides of iron, cerium, chromium, titanium, zinc or zirconium, silicates (e.g. micas), sulfosilicates (e.g. ultramarine) and their combinations, and molecules of an organic nature, such as for example plant extracts. By the term "pearls" are meant special pigments capable of developing reflection and refraction phenomena with light, which may be iridescent or non-iridescent, either organic (such as guanine, CI 75170) or inorganic (such as bismuth oxychloride, CI 77163, or sericite, CI 77019).

Because of the characteristics of the esters of pelargonic acid present in the lipophilic component the cosmetic compositions according to the invention have the particular advantage of ensuring optimum dispersion of the pigments, in particular lipophilic pigments and coated pigments, of which they may help to intensify the colour.

The aqueous cosmetic compositions according to this invention may also contain other additives typically used in the field of cosmetics, such as antioxidants and/or vitamins, sun filters for protection products, preservatives, pH modifiers, moisturisers, conditioners, chelating agents, flow modifiers, texturising agents, film-forming agents, silicones, perfumes, essential oils, and active ingredients, in particular cosmetically and/or dermatologically active ingredients. Each additive may be present in quantities from 0 to 35%, preferably from 0 to 20% by weight, more preferably from 0 to 10%, with respect to the total weight of the cosmetic composition.

By the term "preservatives" according to the invention are meant natural or synthetic substances having the primary function of inhibiting the growth of microorganisms in the cosmetic composition. The list of permitted preservatives makes reference to Appendix V to EC Regulation 1223/2009. The maximum permitted percentages used, any limitations and methods of use may be found within the document. The most widely used preservatives include for example: benzoic acid, propionic acid, salicylic acid, sorbic acid and their salts, p-hydroxybenzoic acid, its salts and esters, dehydroacetic acid, potassium sorbate, phenoxyethanol, imidazolidinyl urea. In combination or as an alternative to the said preservatives the cosmetic compositions according to the invention may also contain other substances capable of contributing to inhibition of the growth of microorganisms such as for example honey, essential oils such as extracts of rosemary, Melaleuca alternifolia and thyme, and complexing agents such as EDTA.

The cosmetic compositions according to some aspects of the invention advantageously comprise one or more flow modifiers. By "flow modifiers" are meant gelling agents, thickening agents, dispersing agents, suspension agents and other substances influencing the rheological behaviour and consequently the stability and application of the cosmetic compositions. They may be of natural or synthetic, mineral or organic origin. Among the organic substances natural polymers such as alginates, carrageens, agar agar, pectin, starches, cellulose and their chemically modified derivatives; synthetic polymers such as acrylic polymers which may or may not have been modified hydrophobically, hydrophobically modified urethanes, alkene/styrene copolymers, polyethylene, polyamides, polyesters, derivatives of polyethylene glycol, ethoxylated fatty alcohols, fatty acids and their salts are preferred. Examples of inorganic flow modifiers are the clays, the silicas and their modified derivatives, magnesium and/or aluminium silicates.

The cosmetic compositions according to some aspects of the invention advantageously comprise one or more moisturisers. Examples of moisturisers are glycerine, sorbitol, glycols or polyethylene glycols.

The cosmetic compositions according to this invention may be in solid, paste or liquid form. The cosmetic compositions according to the invention may be prepared according to processes known to those skilled in the art in the cosmetics sector. According to a preferred method of preparation the desired quantity of the ingredients of the composition are mixed in mixers and/or turboemulsifiers of suitable capacity preferably provided with heat-regulating systems so as to operate at suitable temperatures according to the stability and the melting points of the ingredients.

Because of properties of the neopentyl glycol dipelargonate, glycerol tripelargonate, pentaerythritol tetrapelargonate esters and their mixtures, the aqueous cosmetic compositions to which this invention relates are particularly pleasant to the touch and are at the same time characterised by an emollient and liporestoring effect.

They therefore find application in coloured or colourless care and make-up products, sun protection products and products for detergency of the skin and skin annexes. Aqueous compositions in the form of two-phase solutions according to this invention are also suitable for the preparation of products for the removal of make-up.

Examples of possible applications are creams, milks, sun creams, serums, butters, bath foams, shower foams, detergents, shampoos, leave-on products, hair products such as conditioners, colouring agents, leave-ons and make-up products such as foundation creams, fards, mascaras, eyeliners, lipsticks, lip glosses, concealers, or eye shadow.

Preferred applications are creams, milks, serums, colouring agents, lotions, and products for make-up and for sun protection and for the care of the hair and delicate skins.

One aspect of this invention relates to aqueous cosmetic compositions containing neopentyl glycol dipelargonate. The said cosmetic compositions have a light soft and silky touch, and leave an invisible and not very persistent film on the skin and hair. Surprisingly the said compositions have the particular advantage that they allow delicate and light emulsions to be prepared without using volatile silicones, thus appreciably reducing the environmental impact of the cosmetic products.

Another aspect of this invention relates to aqueous cosmetic compositions containing glycerol tripelargonate. The said cosmetic compositions have a light touch and good softness and hydration. They are therefore suitable for example for nutrient but non-unctuous emulsions and hair products.

Another aspect of this invention relates to aqueous cosmetic compositions containing pentaerythritol tetrapelargonate. The said ester has appreciable emollient properties and imparts a rich touch and brilliant effect to cosmetic compositions, leaving a very obvious film on the skin or hair. Thanks to the optimum softness and excellent dispersion of UVA/UVB sun filters, they are particularly suitable for application in rich emulsions such as sun creams and mascaras.

Another aspect of this invention relates to aqueous cosmetic compositions containing at least two esters selected from neopentyl glycol dipelargonate, glycerol tripelargonate and pentaerythritol tetrapelargonate. Anhydrous cosmetic compositions comprising binary or ternary mixtures of the abovementioned esters, such as for example mixtures of neopentyl glycol dipelargonate and glycerol tripelargonate, or mixtures of neopentyl glycol dipelargonate and pentaerythritol tetrapelargonate, or mixtures of glycerol tripelargonate and pentaerythritol tetrapelargonate, or again mixtures of neopentyl glycol dipelargonate, glycerol tripelargonate and pentaerythritol tetrapelargonate are therefore the object of the invention.

The invention will now be illustrated through the following non-limiting examples.

EXAMPLES

The esters used in the following examples have been prepared using pelargonic acid originating from the oxidative cleavage of sunflower oil having a high oleic acid content. In particular pelargonic acid obtained according to the process described in patent application WO 2011080296 has been used at the end of stage c) of separation of the monocarboxylic acids from the triglycerides containing more than one acid function and subsequent rectification to remove the fraction comprising light monocarboxylic acids, such as described in Example 1. The pelargonic acid used has a purity of 99%.

Preparation of Neopentyl Glycol Dipelargonate, Glycerol Tripelargonate and Pentaerythritol Tetrapelargonate Esters The esterification reactions for synthesis of the three esters were carried out in the absence of catalyst and with a molar excess of pelargonic acid of 30% molar with respect to the polyol used (neopentyl glycol, glycerine or pentaerythritol). In order to favour the removal of esterification water the temperature of the acid/polyol mixtures was increased to 200-210° C. in the course of the reactions; once this temperature had been reached gradual vacuum was applied up to 100 mbar in order to favour conversion of the reagents. Once the reactions were complete, after a quantity of reaction water corresponding to the theoretical quantity had been obtained, the excess acid was recovered by evaporation, keeping the temperature around 180-200° C. with a vacuum of 5 to 10 mbar.

The products then underwent decolouring treatment with activated carbon and decolouring earth and neutralisation through the addition of a quantity of calcium hydroxide and water (in a 1:1 ratio by weight) of between 1 and 2% by weight with regard to each ester, heating to 60° C. with stiffing for 30 minutes. After water had been completely removed by heating to 80-100° C. in a vacuum, a filtering earth (Celite 512; 1% by weight with respect to the ester) was added with stirring, and the liquid was filtered under vacuum on a bed of the same earth, obtaining a clear product.

Measurements of acidity made in accordance with standard ASTM D664 showed a residual acidity of less than 0.1 mg KOH/g for each of the three esters.

The following tables show examples of cosmetic compositions according to the invention. A list of ingredients (in accordance with the INCI nomenclature) and the percentage composition by weight of each ingredient in relation to the total weight of the composition are shown for each composition.

Stability measurements on the compositions obtained were made in accordance with the guidelines shown in UNIPRO Bulletin N.32, by a sensory evaluation of the organoleptic characteristics of the composition (odour, colour, appearance) and the pH was measured by a pH meter after 3 months on samples held at 4° C., 40° C. and ambient temperature/light (25° C.).

Example 1 (Comparison)-2

Aqueous Cosmetic Composition in the Form of a Water-Based Emulsion (Hair Mask/Conditioner)
Ingredients:

| | INCI | Example 1 (comparison) | Example 2 |
|---|---|---|---|
| A | Aqua | 77.05 | 77.05 |
| | Butylene Glycol | 2.00 | 2.00 |
| | Disodium EDTA | 0.10 | 0.10 |
| | Panthenol | 0.50 | 0.50 |
| | Ch0lorphenesin | 0.30 | 0.30 |
| | Sericin | 0.20 | 0.20 |
| | Cetrimonium Chloride | 6.00 | 6.00 |
| B | Cetearyl Alcohol | 6.00 | 6.00 |
| | Ethylhexyl Palmitate | 6.00 | — |
| | Neopentyl glycol dipelargonate | — | 6.00 |
| | Olive Glycerides, Ceramide NP | 0.50 | 0.50 |
| | O-Cymen-5-Ol | 0.10 | 0.10 |
| | Tocopheryl Acetate | 1.00 | 1.00 |
| C | Parfum | 0.25 | 0.25 |

Preparation:
The ingredients in group A were weighed and mixed in a turboemulsifier with constant stiffing, heating to 70+/−2° C.; the ingredients in group B were weighed and mixed in a melter at the same temperature. Mixture B was then placed in mixture A under vacuum; after vacuum had been restored the system was kept stirred and at temperature until emulsification was complete. Still with constant stiffing, the system was then cooled to 35+/−2° C. and ingredient C was added, stirring continuing for a sufficient time to ensure homogeneous mixing. Once the specifications had been checked, the product was cooled to ambient temperature and emptied into suitably arranged containers.

Both the compositions obtained were in the form of white emulsions, at a pH of between 4.5 and 5, and demonstrated the same performance. They also passed the stability test, their organoleptic characteristics and pH remaining unchanged after 3 months at 4° C., 40° C. and 25° C.

Example 3

Aqueous Cosmetic Composition in the Form of a Water-Based Emulsion (Leave-on Product for Hair)
Ingredients:

| | INCI | Example 3 |
|---|---|---|
| A | Aqua | 82.20 |
| | Propylene Glycol, Aqua, *Avena sativa* Kernel Extract | 1.00 |
| | *Citrus Aurantium* Dulcis Fruit Extract | 4.00 |
| | Panthenol | 0.50 |
| | Chlorphenesin | 0.30 |
| | Polyquaternium-47 | 0.30 |
| | Cetrimonium Chloride | 2.00 |
| B | Myristyl Alcohol | 2.00 |
| | Neopentyl glycol dipelargonate | 2.00 |
| | O-Cymen-5-Ol | 0.10 |
| | Tocopheryl Acetate | 0.20 |
| C | Alcohol Denat. | 5.00 |
| D | Parfum | 0.40 |

Preparation:
The ingredients in group A were weighed and mixed in a turboemulsifier with constant stiffing, heating to 70+/−2° C.; the ingredients in group B were weighed and mixed in a melter at the same temperature. Mixture B was then added to mixture A under vacuum, the system being maintained under constant stiffing and temperature conditions. Still with stirring, the system was then cooled to 35+/−2° C. and first component C was added, continuing stirring, and then ingredient D, stiffing being continued until a homogeneous emulsion was obtained. Once the specifications had been checked, the product was cooled to ambient temperature and poured into suitably provided containers.

The compositions were in the form of white low-viscosity emulsions, with a pH of between 4.5 and 5. Organoleptic characteristics and pH remained unchanged after 3 months in stability tests at 4° C., 40° C. and 25° C.

Examples 4 (Comparison)-5

Aqueous Cosmetic Composition in the Form of an Oil-Based Emulsion (Anti-Aging Face Cream)
Ingredients:

| | INCI | Example 4 (comparison) | Example 5 |
|---|---|---|---|
| A | Aqua | 71.40 | 71.40 |
| | Glycerin | 3.00 | 3.00 |
| | Disodium EDTA | 0.10 | 0.10 |
| | Panthenol | 1.00 | 1.00 |
| | Chlorphenesin | 0.30 | 0.30 |
| | *Citrus Nobilis* Fruit Extract | 4.00 | 4.00 |
| | Sodium Hyaluronate | 0.10 | 0.10 |
| B | Caprylic/capric Triglyceride | 2.00 | 2.00 |
| | C12-15 Alkyl Benzoate + Cyclopentasiloxane + Isononyl Isononanoate | 12.00 | — |
| | Neopentyl glycol dipelargonate | — | 12.00 |
| | Tocopherol | 0.30 | 0.30 |
| | O-Cymen-5-Ol | 0.10 | 0.10 |
| | Bisabolol | 0.50 | 0.50 |
| | Polyacrylate Crosspolymer-6 | 0.50 | 0.50 |
| | Sodium Acrylate/ Acryloyldimethyltaurate dimethylacrylamide Crosspolymer, Isohexadecane, Polysorbate 60 | 4.00 | 4.00 |

-continued

| INCI | Example 4 (comparison) | Example 5 |
|---|---|---|
| C Aqua, Glycerin, *Leucojum Aestivum* Bulb Extract | 0.50 | 0.50 |
| D Parfum | 0.20 | 0.20 |

Preparation:

Mixtures of ingredients A and B were prepared and combined in Examples 1-3 and kept stiffing under vacuum at 70+/−° C. The system was then cooled, with constant stirring, to a temperature of 40+/−2° C. and component C was added; once vacuum had been restored, stiffing at constant speed was continued and the system was then cooled to 35+/−2° C. for the addition of ingredient D, stiffing continuing until the mixture was homogeneous. Once the specifications had been checked, the product was cooled to ambient temperature and poured into suitably provided containers.

The use of Neopentyl glycol dipelargonate in Example 5 made it possible to obtain a product having functional and sensory performance comparable with that of the composition of Example 4 in comparison, in which the same quantity by weight (12%) comprised C12-C15 alkyl benzoate, isononyl isononanoate, and cyclopentasiloxane. Organoleptic properties and pH of both compositions remained unchanged in the 3 months' stability tests at 4° C., 40° C. and 25° C.

Examples 6 (Comparison)-7

Aqueous Cosmetic Composition in the Form of an Oil-Based Emulsion (Protective and Soothing Cream, Baby Care).

Ingredients:

| INCI | Example 6 (comparison) | Example 7 |
|---|---|---|
| A Aqua | 71.10 | 71.10 |
| Disodium EDTA | 0.15 | 0.15 |
| Glycerin | 1.50 | 1.50 |
| Octyldodecanol | 1.80 | 1.80 |
| Chlorphenesin | 0.30 | 0.30 |
| Allantoin | 0.30 | 0.30 |
| Sericin | 0.10 | 0.10 |
| Panthenol | 0.30 | 0.30 |
| Sodium Hyaluronate | 0.20 | 0.20 |
| B Xanthan Gum | 0.15 | 0.15 |
| C PEG-6 Stearate, Glycol, Stearate, PEG-32 Stearate | 6.00 | 6.00 |
| Cetearyl Alcohol | 1.60 | 1.60 |
| Glyceryl Stearate | 1.50 | 1.50 |
| *Theobroma Grandiflorum* Seed Butter | 2.00 | 2.00 |
| Cetyl Palmitate | 1.50 | 1.50 |
| *Prunus Amygdalus Dulcis* Oil | 5.00 | 5.00 |
| Dimethicone | 2.00 | — |
| Neopentyl glycol dipelargonate | — | 2.00 |
| O-Cymen-5-Ol | 0.10 | 0.10 |
| Tocopheryl Acetate | 0.20 | 0.20 |
| C15-19 Alkane | 3.00 | 3.00 |
| D Aqua, *Chondrus Crispus* Extract | 1.00 | 1.00 |
| E Parfum | 0.20 | 0.20 |

Preparation:

The ingredients in group A were weighed and mixed in a turboemulsifier with constant stiffing, heating to 75+/−2° C.; ingredient B was weighed separately and was then added to mixture A, then kept stirred again under vacuum by operating the turbine. The ingredients in group C were weighed out and mixed in a melter for fats with gentle stiffing up to a temperature of 75+/−2° C. Mixture C was then added to mixture A+B under vacuum. Vacuum was restored to the system and it was kept stirred, and then cooled with constant stirring to 40+/−2° C. Ingredients D were added at that temperature, and then mixed after vacuum had been restored, and subsequently cooled to 35+/−2° C. Ingredient E was then added, and stiffing was continued until a homogeneous mixture was obtained.

Once the specifications had been checked, the product was cooled to ambient temperature and poured into suitably provided containers.

The use of Neopentyl glycol dipelargonate in Example 7 made it possible to obtain a product having functional and sensory performance comparable to that of the composition of Example 6 in comparison, in which the same quantity by weight (2%) comprised silicone (dimethicone). Both the compositions passed the 3 months' stability test at 4° C., 40° C. and 25° C.

Examples 8 (Comparison)-9

Aqueous Cosmetic Composition in the Form of a Water-Based Emulsion (SPF30 Sun Milk) Ingredients:

| INCI | Example 8 (comparison) | Example 9 |
|---|---|---|
| A Aqua | 62.70 | 62.70 |
| Aqua, Beta Glucan, Gluconolactone, Sodium Benzoate, Calcium Gluconate | 0.50 | 0.50 |
| *Citrus Aurantium Bergamia* Fruit Extract | 3.00 | 3.00 |
| Chlorphenesin | 0.30 | 0.30 |
| Sodium Hyaluronate | 0.10 | 0.10 |
| B Xanthan Gum | 0.30 | 0.30 |
| C Octocrylene | 10.00 | 10.00 |
| Butyl Methoxydibenzoylmethane | 5.00 | 5.00 |
| Ethylhexyl Methoxyccinamate | 5.00 | 5.00 |
| Benzophenone-3 | 5.00 | 5.00 |
| Tocopherol | 0.30 | 0.30 |
| O-Cymen-5-Ol | 0.10 | 0.10 |
| Diisostearyl Malate | 5.00 | — |
| Pentaerythritol tetrapelargonate | — | 5.00 |
| D Hydroxyethyl Acrylate/Sodium Acryloyldimethyl Taurate Copolymer, Polyisobutene, PEG-7 Trimethylolpropane Coconut Ether, Aqua | 2.40 | 2.40 |
| E Parfum | 0.30 | 0.30 |

Preparation:

The ingredients in group A were weighed and mixed in a turboemulsifier with constant stiffing, heating to 60+/−2° C.; ingredient B was weighed separately and then added to mixture A, mixing again in vacuum by operating the turbine. Component D was weighed separately and then added to mixture A+B, mixing all the time. The ingredients in group C were weighed and mixed in a melter for fats with gentle stirring to a temperature of 60+/−2° C. Mixture C was then added to mixture A+B+D under vacuum. Stirring was continued after vacuum had been restored, keeping the turbine in operation; the system was then cooled with stiffing only to 35+/−2° C. Ingredient E was added at that temperature, and stirring was continued until a homogeneous mixture was obtained.

The compositions had a pH of 6-6.5 and passed the 3 months' stability tests at 4° C., 40° C. and 25° C.

The use of Pentaerythritol tetrapelargonate in Example 9 made it possible to obtain a product having functional and sensory performance comparable to that of the composition of Example 8 in comparison, in which the same quantity by weight (5%) comprised diisostearyl malate, demonstrating the same ability to disperse the UVA/UVB filters.

Example 10 (Comparison)-11

Aqueous Cosmetic Composition in the Form of an Oil-Based Emulsion (Baby Ointment/Lotion).
Ingredients:

|   | INCI | Example 10 (comparison) | Example 11 |
|---|---|---|---|
| A | Aqua | 60.10 | 60.10 |
|   | Hydroxyethylcellulosa | 0.50 | 0.50 |
|   | Magnesium Sulfate | 1.00 | 1.00 |
|   | Panthenol | 0.50 | 0.50 |
|   | Glycerin | 5.00 | 5.00 |
|   | Chlorphenesin | 0.30 | 0.30 |
|   | Aqua, Propylene Glycol, *Chamomilla Recutita* Flower Extract | 2.00 | 2.00 |
| B | Polyglyceryl-3 Pentaolivate | 5.50 | 5.50 |
|   | *Simmondsia Chinensis* Seed Oil | 10.00 | 10.00 |
|   | Octyldodecanol | 4.00 | — |
|   | Pentaerythritol tetrapelargonate | — | 4.00 |
|   | Bisabolo | 0.20 | 0.20 |
|   | Tocopherol | 0.50 | 0.50 |
|   | O-Cymen-5-Ol | 0.10 | 0.10 |
|   | *Butyruspermum Parkii* Butter | 10.00 | 10.00 |
| C | Parfum | 0.30 | 0.30 |

Preparation:

The ingredients in group B were weighed and mixed in a turboemulsifier with constant stiffing, heating to 60+/−2° C.; the ingredients in group A were weighed and mixed in a melter at the same temperature. After the pH value of mixture A had been checked, mixture A was then very slowly added to mixture B under vacuum. After vacuum had been restored the system was kept stirred at temperature until an emulsion was obtained. The system was then cooled to 35+/−2° C., with stirring only, and ingredient C was added, stirring being continued until a homogeneous mixture was obtained. Once the specifications had been checked the product was cooled to ambient temperature and poured into suitably provided containers.

The use of Pentaerythritol tetrapelargonate in Example 11, made it possible to obtain a product having functional and sensory performance comparable with that of the composition of Example 10 in comparison, in which the same quantity by weight (4%) comprised octyldodecanol. Both the compositions passed the 3 months' stability tests at 4° C., 40° C. and 25° C.

Example 12

Aqueous Cosmetic Composition in the Form of an Oil-Based Emulsion (Mascara)
Ingredients:

|   | INCI | Example 12 |
|---|---|---|
| A | Cera Alba | 6.5 |
|   | Stearic Acid | 5.51 |
|   | *Copernicia Cerifera* (Carnauba) Wax | 4 |
|   | Pentaerythritol tetrapelargonate | 4 |
|   | Hydrogenated Polycyclopentadiene, Isododecane | 4 |
|   | Mica, Titanium Dioxide (CI77891), Pigment black (CI77499) | 4 |
|   | Synthetic Beeswax | 3 |
|   | *Prunus amygdalus* Dulcis Oil | 1 |
| B | Aqua | 51.19 |
|   | Colorante (CI 77499) | 8 |
|   | Butylene Glycol | 2 |
|   | VP/VA Copolymer | 2 |
|   | Hydroxyethyl Cellulosa | 0.5 |
| C | Triethanolamine | 3 |
| D | Aqua, Benzyl Alcohol, Dehydroacetic Acid | 1 |
|   | Tocopheryl Acetate | 0.3 |

Preparation:

The ingredients in group A were weighed and mixed in a turboemulsifier with constant stiffing, heating to 85° C. The ingredients in group B were weighed separately, mixed and heated to the same temperature. Mixture B was then added to the turboemulsifier with continuous stirring until the preparation was completely emulsified. The mixture was cooled with continuous stiffing and neutralised by adding TEA (ingredient C), the remaining ingredients (D) being added at a temperature below 60° C.

A black pearlescent mascara of pH between 6.5 and 7 was obtained. The product passed the 3 months' stability tests at 4° C., 40° C. and 25° C.

Examples 14 (Comparison) and 15-17

Aqueous Cosmetic Composition in the Form of Water Based Emulsion (Hydrating Dream).
Ingredients:

|   | INCI | Example 14 (comparison) | Example 15 | Example 16 | Example 17 |
|---|---|---|---|---|---|
| A | Aqua | 75.40 | 75.40 | 75.40 | 75.40 |
|   | Disodium EDTA | 0.10 | 0.10 | 0.10 | 0.10 |
|   | Propylene Glycol | 1.00 | 1.00 | 1.00 | 1.00 |
|   | Allantoin | 0.50 | 0.50 | 0.50 | 0.50 |
|   | Chlorphenesin | 0.30 | 0.30 | 0.30 | 0.30 |
| B | Carbomer | 0.50 | 0.50 | 0.50 | 0.50 |
| C | Ceteareth-30 | 5.00 | 5.00 | 5.00 | 5.00 |
|   | Arachhydyl Alcohol, Behenyl Alcohol, Arachydyl Glucoside | 4.00 | 4.00 | 4.00 | 4.00 |
|   | *Argaria Spinosa* Kernel Oil, C10-C18 Triglycerides | 3.0 | 3.0 | 3.0 | 3.0 |
|   | Ethyl hexyl stearate | 7.00 | — | — | — |
|   | Neopentyl glycol dipelargonate | — | 7.00 | — | — |
|   | Glycerol tripelargonate | — | — | 7.00 | — |
|   | Pentaerythritol tetrapelargonate | — | — | — | 7.00 |

-continued

| INCI | Example 14 (comparison) | Example 15 | Example 16 | Example 17 |
|---|---|---|---|---|
| O-Cymen-5-Ol | 0.10 | 0.10 | 0.10 | 0.10 |
| Tocopheryl Acetate | 0.10 | 0.10 | 0.10 | 0.10 |
| D Aqua, | 1.50 | 1.50 | 1.50 | 1.50 |
| Triethanolamine | 0.50 | 0.50 | 0.50 | 0.50 |
| E Parfum | 0.20 | 0.20 | 0.20 | 0.20 |
| F *Aloe barbadensis* Leaf Juice | 0.80 | 0.80 | 0.80 | 0.80 |

Ethyl hexyl stearate of comparative Example 14 was substituted by the same amount (7.00%) of neopentyl glycol dipelargonate in Ex. 15, glycerol tripelargonate in Ex. 16, and pentaerythritol tetrapelargonate in Ex. 17.

The four resulting emulsions were subjected to a sensory evaluation. A panel of 20 female individuals was required to spread each composition on the back of the hand and provide a rating from 1 (low) to 3 (high) on the properties listed in the table below.

The compositions comprising neopentyl glycol dipelargonate and glycerol tripelargonate showed higher softness, smoothness and absorption rate when compared to ethyl hexyl stearate. The composition comprising pentaerythritol tetrapelargonate was the richest and showed the highest film-forming effect.

| Sensory evaluation | Example 14 (Ethyl hexyl stearate) | Example 15 (Neopentyl glycol dipelargonate) | Example 16 (Glycerol tripelargonate) | Example 17 (Pentaerythritol tetrapelargonate) |
|---|---|---|---|---|
| Softness | 2 | 3 | 3 | 2 |
| Smoothness | 1 | 3 | 2 | 1 |
| Greasiness | 3 | 1 | 2 | 3 |
| Stickiness | 3 | 1 | 1 | 3 |
| Film-forming effect | 2 | 2 | 1 | 3 |
| Absorption rate | 1 | 2 | 3 | 1 |

Example 18—Pigments Dispersion

Black Iron Oxide particles (CI77499, commercially available as YPC335200 from Yipin) were dispersed in each of the ester oils of the present invention and in ester oil commonly used as cosmetic ingredients. Each sample of powder particles was wetted by the dropwise addition of one ester oil and then vigorously blended using a spatula until the wet point and the flow point were reached.

The wet point is defined as the minimum volume of dispersant solution to produce a soft coherent mass; the further minimum addition of dispersant solution to produce flow or falling off of the homogeneous mass from the vertical blade of a horizontally held spatula determines the flow point.

The amounts of dispersant solution (i.e. ester oil) needed to reach the wet point (Wp) and the flow point (Fp) were recorded and reported in the table below, expressed in grams per 100 g of pigment.

| Pigment dispersion | Wp (g) | Fp (g) |
|---|---|---|
| Isononyl Isononanoate | 50.00 | 145.00 |
| Caprylic/Capric Triglyceride | 60.00 | 130.00 |
| C12-15 Alkyl Benzoate | 60.00 | 143.00 |
| Neopentyl glycol dipelargonate | 61.00 | 166.00 |
| Glycerol tripelargonate | 60.00 | 100.00 |
| Pentaerythritol tetrapelargonate | 62.00 | 132.00 |

The ester oils of the invention showed dispersion properties comparable to those of commonly used cosmetic ingredients. Surprisingly, glycerol tripelargonate has revealed a Fp significantly close to the Wp, demonstrating dispersion properties even better than those of Caprylic/Capric Triglyceride. This minimum difference results in a considerable advantage as it enables significant cost savings on the final composition (wherein about 30% less solvent is required).

The dispersions thus prepared were tested on the forearm by a panel of 20 individuals to assess the differences in terms of smoothness, writing capabilities, color consistency, gloss effect. A scale from 1 (low) to 5 (high) was used. The sensory evaluation test results are reported in the table below.

| Sensory evaluation | Isononyl Isononanoate | Caprylic/ Capric Triglyceride | C12-15 Alkyl Benzoate | Neopentyl glycol dipelargonate | Glycerol tripelargonate | Pentaerythritol tetrapelargonate |
|---|---|---|---|---|---|---|
| Flowability | 4 | 4 | 2 | 2 | 5 | 4 |
| Writing capability/ color intensity | 2 | 4 | 4 | 3 | 4 | 4 |
| Film evenness | 2 | 3 | 4 | 4 | 4 | 4 |
| Gloss effect | 2 | 3 | 4 | 2 | 5 | 5 |

Glycerol tripelargonate and pentaerythritol tetrapelargonate showed flowability, film evenness and gloss effect higher than those of commonly used ester oils.

Example 19—UV Filters Dispersion

The dispersibility of a solid UV filter in different ester oils was tested using Titania (TiO$_2$, commercially available as Titanio Biossido Anatasio from A.C.E.F.). Various ratios of filter/ester (1% and 10% TiO$_2$) were prepared under stiffing at 70° C. for 30 minutes. The dispersions were then observed after a storage period of 0 hours ($t_0$) and 24 hours ($t_{24}$) at ambient temperature (25° C.) to check for the formation of any sediment deposit. Results for each ester are shown in the table below (D=homogeneous dispersion; S=sediment deposit).

| Filters dispersion | $t_0$ | | $t_{24}$ | |
|---|---|---|---|---|
| | 1% | 10% | 1% | 10% |
| Isononyl Isononanoate | D | D | S | S |
| Caprylic/Capric Triglyceride | D | D | S | S |
| C12-15 Alkyl Benzoate | D | D | S | S |
| Neopentyl glycol dipelargonate | D | D | S/D | S/D |
| Glycerol tripelargonate | D | D | D | S/D |
| Pentaerythritol tetrapelargonate | D | D | D | D |

The dispersant capability of the pelargonic acid esters of the invention was equivalent than that of commonly used esters such as Isononyl Isononanoate, Caprylic/Capric Triglyceride and C12-15 Alkyl Benzoate.

Glycerol tripelargonate and pentaerythritol tetrapelargonate showed an even better dispersion of Titania compared with reference solvents.

Example 20—UV Filters Solubility

The solubility of the chemical UV filter Butyl methoxydibenzoylmethane (CAS No 70356-09-1, commercially available as PARSOL® 1789 from DSM) in different ester oils was tested. Various ratios of solute/solvent (5%, 10%, 20% and 30% by weight; total amount filter+solvent: 10 g) were prepared in glass bottles in a water bath at 60° C. The solutions were then observed after a storage period of 2 hours at 20° C. to check for the formation of any sediment deposit. Once identified the solubility range, which ranged between 10-20% for each filter/solvent couple, the maximum concentration of soluble filter in each ester was determined by making repeated additions of lower amounts of the filter to the solutions at 10%, until the formation of precipitate was observed. Each addition was carried out at a temperature of 60° C. and followed by cooling. The solutions were allowed to stand at the constant temperature of 20° C. for two hours before checking for precipitation (by visual determination).

Results for each ester are shown in the table below:

| Filters solubility | % w/w, 20° C. |
|---|---|
| Caprylic/Capric Triglyceride | 14 |
| C12-15 Alkyl Benzoate | 14 |
| Neopentyl glycol dipelargonate | 18 |
| Glycerol tripelargonate | 18 |
| Pentaerythritol tetrapelargonate | 18 |

The solubility values of Butyl methoxydibenzoylmethane in the three pelargonic acid esters at 20° C. was equivalent and considerably higher than that in commonly used esters such as Caprylic/Capric Triglyceride and C12-15 Alkyl Benzoate.

Example 21—UV Filters Solubility

The solubility of the chemical UV filter Benzophenone-3 (CAS No 131-57-7, commercially available as UVASORB® MET from 3V Sigma) in pentaerythritol tetrapelargonate and in a ternary mixture of neopentyl glycol dipelargonate, glycerol tripelargonate and pentaerythritol tetrapelargonate (in a weight ratio of 1:1:1) was determined at 20° C. as described in Example 20.

The solubility value of Benzophenone-3 in pentaerythritol tetrapelargonate was of 14% w/w at 20° C., while the corresponding solubility value of the same filter in the ternary mixture was of 19% w/w. The mixture of pelargonic acid esters according to the invention therefore revealed a surprisingly high ability to solubilize UV filters when compared to the one of the individual ester.

The invention claimed is:

1. A cosmetic composition comprising at least 20% by weight of an aqueous component and a lipophilic component in the form of water in oil emulsion, oil in water emulsion or having the aqueous component separate from the lipophilic component in two separate layers (biphasic form), wherein the said lipophilic component comprises of neopentylglycol dipelargonate.

2. The cosmetic composition according to claim 1 comprising from 0.1% to 50% by weight of neopentylglycol dipelargonate, relative to the weight of the cosmetic composition.

3. The cosmetic composition according to claim 2 comprising at least neopentylglycol dipelargonate.

4. The cosmetic composition according to claim 2 in the form of a water-in-oil emulsion, and comprising up to 50% by weight of a lipophilic component comprising at least an ester of neopentylglycol dipelargonate.

5. The cosmetic composition according to claim 1 in the form of a water-in-oil emulsion, and comprising up to 50% by weight of a lipophilic component comprising at least an ester of neopentylglycol dipelargonate.

6. The cosmetic composition according to claim 1 comprising, relative to the total weight of the cosmetic composition:
   (a) from 35 to 80% by weight of an aqueous phase;
   (b) from 10% to 50% by weight of a lipophilic component comprising at least an ester of neopentylglycol dipelargonate; and
   (c) from 0.3% to 15% by weight of one or more emulsifying agents with HLB from 3 to 6.

7. The cosmetic composition according to claim 1 in the form of an oil-in water emulsion, and comprising up to 40% by weight of a lipophilic component comprising at least an ester of neopentylglycol dipelargonate.

8. The cosmetic composition according to claim 7 comprising, relative to the total weight of the cosmetic composition:
   (a) from 60 to 90% by weight of an aqueous phase;
   (b) from 0.5% to 40% by weight of a lipophilic component comprising at least an ester of neopentylglycol dipelargonate; and
   (c) from 5% to 15% of one or more emulsifying agents with HLB from 6 to 12.

9. The cosmetic composition according to claim 1 and comprising up to 15% by weight of a lipophilic component comprising at least an ester of neopentylglycol dipelargonate.

10. The cosmetic composition according to claim 9, relative to the total weight of the cosmetic composition:
    (a) from 60 to 90% by weight of an aqueous phase;
    (b) from 0.5% to 15% by weight of a lipophilic component comprising at least an ester of neopentylglycol dipelargonate; and
    (c) from 8% to 40% by weight of one or more surfactants.

11. The cosmetic composition according to claim 1 in biphasic form comprising, relative to the total weight of the cosmetic composition:
    (a) from 50 to 70% by weight of an aqueous phase; and
    (b) from 30% to 50% by weight of a lipophilic component comprising at least an ester of neopentylglycol dipelargonate.

12. The cosmetic composition according to claim 1 wherein the said lipophilic component further comprises at least one oil selected from esters, ethers, alcohols and hydrocarbons of natural and/or synthetic origin, silicone oils, or mixtures thereof.

13. The cosmetic composition according to claim 1 in the form of emulsion wherein the lipophilic component further comprises a butter and/or wax.

14. The cosmetic composition according to claim 1 comprising one or more sun filters in quantities from 0.1% to 35% by weight.

15. The cosmetic composition according to claim 1 comprising one or more colouring agents and/or one or more additives selected from antioxidants and/or vitamins, preservatives, pH modifiers, humectants, conditioners, chelating agents, flow modifiers, texturizers, film-forming agents, silicones, perfumes, essential oils or active principles.

16. The cosmetic composition according to claim 15 wherein each of said colouring agents and/or additives is present in amounts from 0 to 35% by weight with respect to the total weight of the cosmetic composition.

17. The cosmetic composition according to claim 1 for use in the protection from the sun of skin and skin appendages.

18. A method for the care, for make-up or for the cleansing of the skin or skin appendages which comprises applying to the skin or skin appendages a cosmetic composition according to claim 1.

19. A method for the preparation of a composition selected from the group consisting of creams, milks, serums, butters, bath foams, shower foams, shower gels, detergents, shampoos, leave-on, balms, hair masks and leave-on, conditioners, foundations, and mascaras, wherein said composition comprising at least 20% by weight of an aqueous component and wherein the method comprises including in said composition a lipophilic component in the form of water in oil emulsion, oil in water emulsion or having the aqueous component separate from the lipophilic component in two separate layers (biphasic form) wherein the lipophilic component comprises at least one ester of neopentylglycol dipelargonate.

* * * * *